United States Patent [19]

Ryer et al.

[11] 4,199,463
[45] Apr. 22, 1980

[54] ALKYLENE GLYCOL ESTERS OF CARBOXYLATE HALF ESTERS OF 1-AZA-3,7-DIOXABICYCLO[3.3.0] OCT-5-YL METHYL ALCOHOLS, THEIR PREPARATION AND USE AS ADDITIVES FOR GASOLINE AND MIDDLE DISTILLATE FUELS AND LUBRICANTS

[75] Inventors: Jack Ryer, East Brunswick; Stanley Brois, Westfield; Esther D. Winans, Colonia, all of N.J.

[73] Assignee: Exxon Research & Engineering Co., Florham Park, N.J.

[21] Appl. No.: 5,311

[22] Filed: Jan. 22, 1979

Related U.S. Application Data

[60] Continuation-in-part of Ser. No. 952,475, Oct. 18, 1978, abandoned, which is a continuation-in-part of Ser. No. 752,872, Dec. 20, 1976, abandoned, which is a division of Ser. No. 573,545, May 1, 1975, Pat. No. 4,017,406.

[51] Int. Cl.$^2$ .......................... C10M 1/32; C10L 1/22
[52] U.S. Cl. ................... 252/51.5 A; 44/63; 252/51.5 R; 548/218
[58] Field of Search ............ 252/51.5 A, 51.5 R; 44/63; 260/307 FA

[56] References Cited

U.S. PATENT DOCUMENTS

| | | | |
|---|---|---|---|
| 2,448,890 | 9/1948 | Johnston | 260/307 FA |
| 3,455,831 | 7/1969 | Davis | 44/63 X |
| 3,632,511 | 1/1972 | Liao | 44/63 X |
| 3,759,942 | 9/1973 | Himics | 260/307 FA |
| 3,864,335 | 2/1975 | Emmons | 260/307 FA |
| 4,049,564 | 9/1977 | Ryer et al. | 252/51.5 A |
| 4,102,798 | 7/1978 | Ryer et al. | 252/51.5 A |

FOREIGN PATENT DOCUMENTS

| | | | |
|---|---|---|---|
| 809001 | 2/1959 | United Kingdom | 252/51.5 A |
| 984409 | 2/1965 | United Kingdom | 252/51.5 A |

*Primary Examiner*—Andrew Metz
*Attorney, Agent, or Firm*—Roland A. Dexter

[57] ABSTRACT

Alkylene glycol esters of carboxylate half esters of 1-aza-3,7-dioxabicyclo[3.3.0] oct-5-yl methyl alcohols which are the reaction products of organic acid materials, preferably long chain dicarboxylic anhydrides such as octadecenyl and polyisobutenylsuccinic anhydrides and aldehyde/tris [hydroxymethyl] aminomethane (THAM) adducts or mixtures are friction reducing additives for liquid hydrocarbons, such as gasoline middle distillates and lubricants.

10 Claims, No Drawings

ALKYLENE GLYCOL ESTERS OF CARBOXYLATE HALF ESTERS OF 1-AZA-3,7-DIOXABICYCLO[3.3.0] OCT-5-YL METHYL ALCOHOLS, THEIR PREPARATION AND USE AS ADDITIVES FOR GASOLINE AND MIDDLE DISTILLATE FUELS AND LUBRICANTS

CROSS-REFERENCE TO RELATED APPLICATIONS

This application is a continuation-in-part of Ser. No. 952,475 filed Oct. 18, 1978 now abandoned, which is a continuation-in-part of Ser. No. 752,872, filed Dec. 20, 1976 now abandoned, which in turn is a divisional of Ser. No. 573,545, filed May 1, 1975 now U.S. Pat. No. 4,017,406.

BACKGROUND OF THE INVENTION

1. Field of the Invention

The invention relates to novel oil-soluble alkylene glycol esters of partial esters derived from the reaction or organic acid materials such as dicarboxylic acids or anhydrides and an aldehyde/tris-(hydroxymethyl) aminomethane adduct or mixture. These novel oil-soluble alkylene glycol ester derivatives have utility as friction reducing additives for hydrocarbon fuels and lubricating oils.

2. Description of Prior and Related Art

There are two principle environments which are encountered by automotive crankcase lubricants, i.e. cyclical high and low temperatures from stop-and-go driving and continuous high temperatures from extended operation of the automobile over long distances. Each of these environments provokes the presence in the lubricant of varying proportions of foreign particles such as dirt, soot, water and decomposition products resulting from breakdown of the oil. This foreign matter appears responsible for the deposition of a mayonnaise-like sludge which circulates with the oil.

During the past decade, ashless sludge dispersants have become increasingly important, primarily in improving the performance of lubricants in keeping the engine clean of deposits and permitting extended crankcase oil drain periods while avoiding the undesirable environmental impact of the earlier used metal-containing additives. One commercial type of ashless dispersant contains nitrogen resulting from the attachment of an amine or polyamine to a long-chain hydrocarbon polymer (the oil solubilizing portion of the molecule), usually polyisobutylene through an acid group, e.g. polyisobutenyl succinic anhydride, by forming amide or imide linkages. Specifically such additives include: (a) lubricating oil detergents of the Schiff base type are prepared by reacting alkenyl succinic acid anhydride and a polyamine to provide an imide intermediate subsequently reacted with an aldehyde (see U.S. Pat. No. 3,455,831); (b) United Kingdom Specificiation No. 809,001 teaches corrosion inhibitors comprising a multiple salt complex derived from the reaction product of hydrocarbyl substituted dicarboxylic acids and hydroxy amines (including 2-amino-2-methyl-1,3-propanediol [AMP] and trishydroxy methylaminomethane (hereafter designated THAM) further complexed with mono- and polycarboxylic acids; (c) U.S. Pat. No. 3,632,511 teaches reacting polyisobutenylsuccinic anhydride with both a polyamine and a polyhydric alcohol including THAM; and, (d) United Kingdom Specification No. 984,409 teaches ashless, amide/imide/ester type lubricant additives prepared by reacting an alkenyl succinic anhydride, with a hydroxy amine including THAM.

In the operation of an internal combustion engine, there are many "Boundary Lubrication" conditions where two rubbing surfaces must be lubricated, or otherwise protected so as to prevent wear and to insure continued movement. Moreover, where, as in most cases, friction between the two surfaces will increase the power required to effect movement and where the movement is an integral part of an energy conversion system, it is most desirable to effect the lubrication in a manner which will minimize this friction and/or reduce wear. As is also well known, both wear and friction can be reduced, with various degrees of success, through the addition of a suitable additive or combination thereof, to a natural or synthetic lubricant. Similarly, continued movement can be insured, again with varying degrees of success, through the addition of one or more appropriate additives.

While there are many known lubricant additives which may be classified as antiwear, antifriction and extreme pressure agents and some may in fact satisfy more than one of these functions as well as provide other useful functions, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates, e.g. the zinc dialkyl dithiophosphates, are one of the additives which are known to exhibit antioxidant and antiwear properties. While they afford excellent oxidation resistance and exhibit superior antiwear properties, it has heretofore been believed that the same increases or significantly limits their ability to decrease friction between moving surfaces. As a result, compositions containing zinc dialkyl dithiophosphates were not believed to provide the most desirable lubricity and, in turn, it was believed that use of compositions containing the same would lead to significant energy losses in overcoming friction even when antifriction agents are included in the composition.

Known ways to solve the problem of energy losses due to high friction in crankcase lubrication include the use of synthetic ester base oils which are expensive and the use of insoluble molybdenum sulfide and graphite dispersions which have the disadvantage of giving the oil composition a black or hazy appearance.

SUMMARY OF THE INVENTION

It has now been discovered that novel hydrocarbon soluble alkylene glycol esters of partial, i.e. half, esters of 1-aza-3,7-dioxabicyclo[3.3.0] oct-5-yl methyl alcohols (hereafter designated DOBO) can be formed by the ethoxylation of the product of the reaction or organic dicarboxylic acids and anhydrides, with an aldehyde-(THAM) adduct or aldehyde-(THAM) mixture. For liquid hydrocarbon compositions wherein the alkylene glycol esters of the invention have been found to be highly useful as friction reducing additives, the carbon chain length is from $C_6$ to $C_{50}$ carbon atoms for fuels such as gasoline and middle distillates, that is from 6 to 30 carbon atoms for gasoline and from 6 to 50 carbon atoms for middle distillate fuels, and from 6 to 150, preferably from 16 to 90, carbons for lubricating oils (solubility in the particular composition is not essential for useful results as a friction reducing additive). The operational embodiment of the invention thus is a composition comprising a major proportion of a liquid hydrocarbon of the class consisting of fuels and lubricating oils and a minor but at least friction reducing amount of a hydrocarbon soluble alkylene glycol ester of a partial ester of 1-aza-3,7-dioxabicyclo[3.3.0] oct-5-yl methyl alcohol, said ethoxylated derivative preferably being from 0.001 to 20 wt.% of said composition.

The alkylene glycol esters are prepared by reacting one to ten moles of an alkylene oxide such as ethylene oxide or propylene oxide with each mole of the half ester of the alkenylsuccinic anhydride-DOBO adduct, although it must be understood that said adduct could be catalytically reacted with a polyalkylene glycol to provide said derivative as will be apparent to one skilled in the art.

The dicarboxylic acid material—DOBO adduct, e.g. the alkenylsuccinic anhydride—DOBO adduct, is the essential precursor from which the alkylene glycol esters of half esters derivatives are obtained. The alkylene glycol ester derivatives of the invention can be characterized by the following formula:

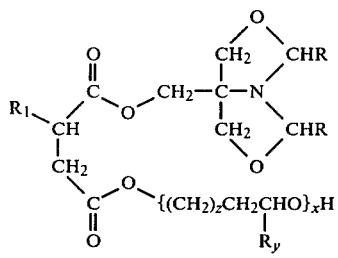

wherein X is 1 to 10 preferably 2 to 4, $R_1$ represents a hydrocarbyl group of 6 to 150 carbons, Z is 0 or 1, R is H, or $C_1$ to $C_{12}$, preferably $C_3$ to $C_8$ hydrocarbyl group and $R_y$ is H or a $CH_3$ (methyl) group.

DICARBOXYLIC ACID MATERIALS

Numerous types of acid materials can be utilized according to this invention, however, dicarboxylic acids which afford liquid hydrocarbon soluble ethoxylated esters from aldehyde/THAM adducts or mixtures are preferred. Especially preferred reactants are aliphatic substituted succinic acid anhydrides.

Any 2-alkyl, 2-alkenyl-2,3-dialkyl or 2,3-cycloalkenyl substituted dicarboxylic acid material, i.e. acid, anhydride or ester e.g., succinic acid anhydride or its corresponding acid, or mixtures thereof can be used in the present invention. The alkyl or alkenyl group can be branched or straight chain, and there is no real upper limit to the number of carbon atoms therein.

It is particularly preferred that the aliphatic substituent in the 2-position of the succinic anhydride is a polymer of $C_2$ to $C_5$ monoolefins, e.g., ethylene, propylene, butylene, isobutylene and pentene. The polymers can be homopolymers such as polyisobutylene and styrene as well as copolymers of two or more of monoolefins such as copolymers of ethylene and propylene, butylene and isobutylene or of propylene and isobutylene.

The polymers will have average molecular weights within the range of about 500 to about 2100, or more usually between about 800 and about 1800. Particularly useful olefin polymers have average molecular weights within the range of about 900 and about 1500 with approximately one double bond per polymer chain.

An especially valuable starting material for a highly potent dispersant additive made in accordance with this invention is polyisobutylene having an average molecular weight in the range of about 900 to about 1500. Molecular weights are conveniently determined by vapor phase osmometry; said determinations being used for all values set forth herein.

The substituted succinic anhydrides are readily available from the reaction of maleic anhydride with polyolefins or with chlorinated polyolefins. Interaction of polyolefins with maleic anhydride [Ene reactions] give polyalkenylsuccinic anhydrides. The olefin polymer can if desired, be first halogenated, for example, chlorinated or brominated to about 2 to 5 wt.% chlorine, or about 4 to 8 wt.% bromine, based on the weight of polymer, and then reacted with the maleic anhydride.

Other halogenation techniques for attaching the dicarboxylic acid material to a long hydrocarbon chain, involve first halogenating the unsaturated dicarboxylic acid material and then reacting with the olefin polymer, of by blowing halogen gas, e.g., chlorine, through a mixture of the polyolefin and unsaturated dicarboxylic acid material, then heating to 150° to 220° C. in order to remove HCl gas.

In summary therefore, the dicarboxylic acid material used in the invention includes alpha-beta unsaturated $C_4$ to $C_{10}$ dicarboxylic acid or anhydrides or esters thereof such as fumaric acid, itaconic acid, maleic acid, maleic anhydride, malic acid, maleamic acid, chloromaleic acid, dimethyl fumarate, etc. These dicarboxylic acid materials are substituted with a hydrocarbon chain containing at least 6 carbons to 150 carbons, preferably from 6 to 90 depending upon the nature of composition into which the additive will be incorporated, that is, for oleaginous compositions such as gasoline and middle distillate fuels, the carbon chain length ranges from 6 to 50 carbons and for lubricating oils from 6 to 150 preferably 16 to 90.

As earlier stated, numerous acids can be reacted with aldehyde/THAM adducts or mixtures. These acids are illustrated by the following types: aromatic acids such as phthalic, mellitic and pyromellitic; and, thio acids such as tridecanethionothiolic.

ALDEHYDE-THAM ADDUCTS

The requisite aldehyde/THAM adducts, more specifically, 1-aza-3,7-dioxabicyclo[3.3.0] oct-5-yl methyl alcohols (I), can be readily prepared by condensing two moles of aldehyde with one mole of THAM (Equation 1) according to the procedures described by M. Senkus in the "Journal of the American Chemical Society", 67, 1515 (1945).

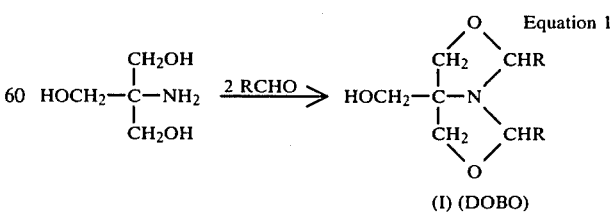

(I) (DOBO)

wherein R=H, $CH_3$, n-$C_3H_7$, n-$C_3H_{11}$, Ph, $PhCH_2$, etc. Thus, a variety of aldehydes such as formaldehyde, acetaldehyde, propionaldehyde, butyraldehyde, isobutyraldehyde, 2-ethylhexanal, dodecyl aldehyde, benzaldehyde, tolualdehyde, anisaldehyde, piperonal, naphthaldehydes, phenylacetaldehyde, furfural, etc., can be condensed with (THAM) to produce symmetrically substituted (I, R=R) aldehyde/THAM adducts.

UNSYMMETRICAL ADDUCTS

In another embodiment of the present invention, unsymmetrical adducts may be prepared by first treating THAM with one mole of an aldehyde or ketone (Equation 2) to generate an oxazolidine product (II) according to procedures described in the literature by E. D. Bergmann, "Chemical Reviews", 53, 309 (1953).

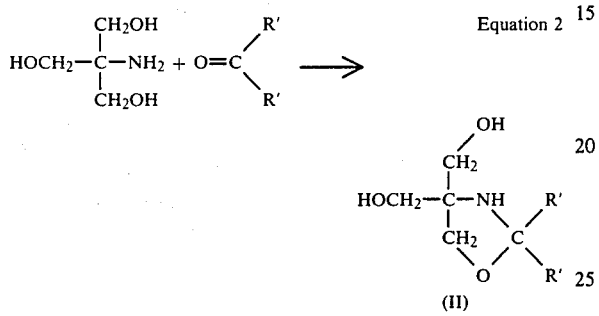

Equation 2

(II)

wherein R' represents a $C_1$ to $C_{35}$ alkyl, cycloalkyl or aryl group and substantially saturated polymeric hydrocarbon groups of 35 to 150 carbons; the longer chain polymeric groups of 50 and more carbons provide dispersancy to lubricating oils. Subsequent treatment of the oxazolidine with a mole of aldehyde such as formaldehyde affords the unsymmetrical adduct III, as depicted in Equation 3.

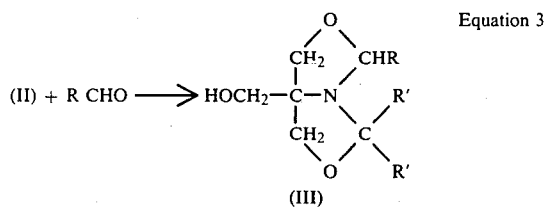

Equation 3

(III)

wherein R and R' are the same as earlier described.

Aldehyde reactants described in the preparation of symmetrically substituted adducts (I) above are suitable for the reactions described in Equation 3.

Numerous types of ketone reactants can be employed in the formation of the oxazolidines (Equation 2) required in the design of unsymmetrically substituted 1-aza-3,7-dioxabicyclo[3.3.0] oct-5-yl methyl alcohols (III). Included in the repertory of useful ketones are acetone, butanone, pentanones, methyl isobutyl ketone, pinacolone, amyl methyl ketone, cyclopentanone, cyclohexanone, acetophenone, etc.

Long chain aldehydes and ketones formed in the oxidation of copolymers of ethylene and propylene, butylene and isobutylene, and ethylene, propylene and 1,4-hexadiene can also be employed. The aldehyde and ketone functionalized polymers will have average molecular weights within the range of about 500 to about 2100, i.e. from 35 to 150 carbons.

In forming unsymmetrical adducts (III) from oxazolidine generated from ketone reactants, a particularly preferred aldehyde is formaldehyde which, owing to its favorable steric requirements, rapidly cyclizes the oxazolidine intermediate to the desired bicyclic structure, III (R=H).

REACTION CONDITIONS FOR HALF ESTER FORMATION

The formation of the half ester intermediates can be effected by reacting a mole of dicarboxylic acid anhydride with a mole of an aldehyde/THAM adduct i.e. equimolar as portrayed in Equation 4 with $R_1$ and R as earlier described.

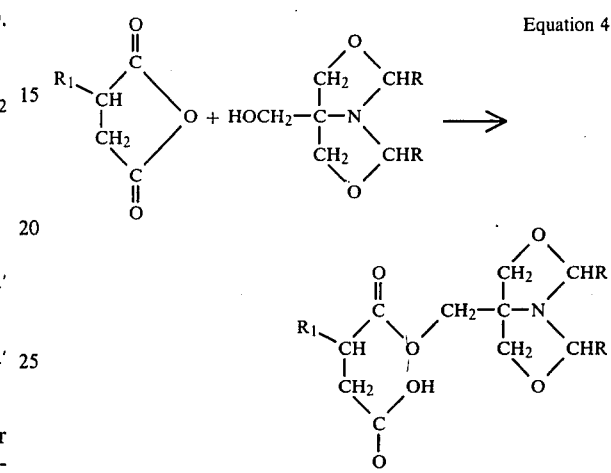

Equation 4

The mode of addition of reactants does not appear to affect product composition, and convenience will usually dictate which reagent is added to the other. Zinc salts such as zinc acetate, chloride, etc., when required, can be employed to catalyze the esterification process. In general, the reaction is effected in a reactor in the absence of or presence of an inert diluent such as xylene and solvent oil and heating the mixture from about 50° C. to about 200° C. preferably 70° C. to 150° C. for about 10 minutes to 48 hours, more preferably 1 to 3 hours. Completion of reaction can be readily discerned by infrared analysis.

The disappearance of the characteristic anhydride carbonyl absorption bands, together with the presence of strong ester and carboxylic acid carbonyl bands indicate that complete esterification has occurred.

In a preferred embodiment of the present invention, the symmetrical adduct can be formed in situ, by heating a mixture of 2 moles of aldehyde and a mole of THAM at about 80° C. to about 210° C. for about 1 to about 4 hours. Quite often infrared analysis can be used to discern complete reaction by the disappearance of the aldehyde carbonyl absorption bond. In instances where unsymmetrical adducts are desired, a mole of aldehyde or ketone is heated with a mole of THAM at about 80° C. to about 210° C. for about 1 to about 24 hours, or until periodic infrared analyses of the reaction mixture show the absence of a carbonyl absorption band. Thereafter, a mole equivalent of aldehyde, preferably formaldehyde is added to the intermediary oxazolidine and the mixture is heated at about 80° C. to about 210° C. for approximately 1 to about 4 hours. The in situ formed adduct can thereafter be reacted with a carboxylic acid or anhydride by adding, for example, a mole of alkenylsuccinic anhydride to the adduct and heating the well-stirred reaction mixture at about 80° C. to about 200° C. for approximately 15 minutes to about 4 hours, or until the infrared spectrum of the reaction mixture reveals the absence of the characteristic anhydride carbonyl absorption bands.

ALKYLENE GLYCOL ESTERS OF CARBOXYLATE HALF ESTERS OF 1-AZA-3,7-DIOXABICYCLO[3.3.0] OCT-5-YL METHYL ALCOHOLS

The alkylene oxides and glycols useful for preparation of the ethoxylated derivatives of the invention are of the group consisting essentially of $C_2$ to $C_3$ alkylene oxides, i.e. ethylene oxide or propylene oxide and glycols of the formula:

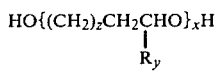

wherein x is 1 to 10, $R_y$ is hydrogen or $CH_3$ (methyl) and z is 0 or 1.

The glycols included herein are diethylene glycol, dipropylene glycol, triethylene glycol, tripropylene glycol, tetraethylene glycol, tetrapropylene glycol and polyethylene glycols and polypropylene glycols of ($M_n$) in the range of 200 to 600.

The alkylene glycol ester derivatives are readily prepared by a reaction with the intermediate dissolved in an inert solvent such as toluene or xylene introducing the alkylene oxide into a pressure vessel containing said solution beneath its surface or adding the desired amount of glycol and refluxing. Usefully, these reactions are carried out at temperatures of from 50° C. to 150° C., preferably 100° C. to 140° C. in the presence of a catalyst until about one molar equivalent of water has been removed from the reaction or infrared analysis shows disappearance of the carboxy carbonyl band located at about 5.8μ.

The following preparations and examples are included therein as further description and illustrative of the present invention.

PREPARATION OF ALDEHYDE-THAM ADDUCTS (DOBO)

EXAMPLE 1

0.1 mole (12.1 g) of THAM was dissolved in an equal weight of water. To the resulting solution in a 250 ml. Erlenmeyer flask equipped with magnetic stirrer was added 0.2 mole (6.0 g) of paraformaldehyde. The stirred mixture was heated to 70° C. to effect dissolution of the paraformaldehyde and continued for 15 minutes at 70° C. to produce the 1-aza-3,7-dioxabicyclo[3.3.0] oct-5-yl methyl alcohol (DOBO) in quantitative yields. The product after evaporation of water and recrystallization from benzene melted at 60°-61° C. and analyzed for 49.12% carbon, 7.52% hydrogen and 9.59% nitrogen.

ESTERIFICATION OF ALDEHYDE-THAM ADDUCT (DOBO)

EXAMPLE 2

HALF ACID ESTER OF 1-AZA-3,7-DIOXABICYCLO[3.3.0] OCT-5-YL METHYL OCTADECENYLSUCCINATE 0.5 mole of octadecenylsuccinic anhydride was added to a 1 liter round bottom flask and heated to 140° C. for an hour to convert any partially hydrolyzed reactant to the anhydride form. After cooling the nitrogen-blanketed reactor to 100° C., 0.5 mole of DOBO was added in one portion. The alcohol reagent readily dissolved and the clear solution was heated to 174° C. for about 2 hours. Infrared analysis showed that esterification was complete at this point. The infrared spectrum of the tan product featured prominent absorption bands at 5.75, 5.85, 8.65, 9.10, 10.3 and 10.7 microns.

Analysis based on $C_{28}H_{50}NO_6$: Calculated: C, 67.70; H, 10.15; N, 2.82. Found: C, 66.57; H, 9.95; N, 2.60.

The product, recrystallized from hexane, melted at 58°-62° C.

EXAMPLE 3

HALF ACID ESTER OF 1-AZA-3,7-DIOXABICYCLO[3.3.0]OCT-5-YL METHYL POLYISOBUTYLENESUCCINATE 0.2 mole (267 g) of polyisobutenylsuccinic anhydride of MW 980 with a Sap. No. of 84 was charged into a 1 liter flask and heated to 180° C. The anhydride reactant is heated at 180° C. under high vacuum for 2 hours to remove any light ends. About 2.8 g of volatiles were collected in a dry ice-cooled receiver. The stirred reactant is then cooled to 120° C., and 0.2 mole (29.0 g) of DOBO plus 1 gram of zinc acetate catalyst are added. The stirred reaction mixture is then heated at 210° C. for several hours until infrared analysis shows complete esterification. An equal weight of neutral oil (S-15ON) is added to the product at about 120° C. The diluted product analyzed for 0.42% nitrogen and featured an infrared spectrum with a dominant absorption band at 5.75 microns.

EXAMPLE 4

HALF ACID ESTER OF 1-AZA-3,7-DIOXA-2,8-DI-N-PROPYLBICYCLO[3.3.0] OCT-5-YL METHYL OCTADECENYL-SUCCINATE 0.27 mole of (94.5 g) of normal octadecenylsuccinic anhydride was added to a 500 ml flask and heated for an hour at 140° C. to convert any partially hydrolyzed reactant to the anhydride form. The reaction was cooled to 70° C. and 0.3 mole (68.7 g) of 1-aza-3,7-dioxa-2,8-di-n-propyl bicyclo[3.3.0] oct-5-yl methyl alcohol was added to the flask and heating was maintained for 1 hour at 98°-104° C. The I.R. spectrum of the product showed disappearance of the anhydride band and the appearance of 2 bands at 5.75 and 5.85 microns.

EXAMPLE 5

HALF ACID ESTER OF 1-AZA-3,7-DIOXA-2,8-DIPHENYLBICYCLO[3.3.0] OCT-5-YL METHYL OCTADECENYL SUCCINATE 0.27 mole (94.5 g) of n-octadecenylsuccinic anhydride was added to a 300 ml. flask and heated for an hour at 140° C. The reaction was cooled to 70° C. and 0.30 moles (89.1 g) of 1-aza-3,7-dioxa-2,8-diphenylbicyclo[3.3.0] oct-5-yl methyl alcohol was added to the flask and heating continued for 1 hour at 107°-114° C. The I.R. spectrum of the product showed the presence of 2 bands at 5.75 and 5.85 microns.

EXAMPLE 6

One mole of the product of Example 2 dissolved in an equal weight of heavy aromatic naphtha was placed in a stainless steel pressure vessel and one mole of ethylene oxide reacted with said product by heating at from 149° C. to 160° C. for 2 hours at 30–40 psig and in the presence of 0.3% by weight of NaOH (present as a catalyst). The product recovered was a mixture of monoethylene glycol and diethylene glycol esters of the half acid ester of 1-dioxabicyclo[3.3.0] oct-5-yl methyl octadecenyl succinate (approximately 1 weight proportion of the monoethylene glycol ester to 2 weight proportions of the diethylene glycol ester).

EXAMPLE 7

The process of Example 6 was followed except that two moles of ethylene oxide was reacted with one mole of said product of Example 2. The resulting ethoxylated derivative was a mixture of monoethylene glycol, diethylene glycol and triethylene glycol esters of the half acid ester of Example 2 (said mixture containing about 90 wt.% diethylene glycol ester, about 10 wt.% ethylene glycol ester and a trace of triethylene glycol ester).

EXAMPLE 8

The process of Example 6 was followed except that three moles of ethylene oxide was reacted with one mole of said product of Example 2 to provide a product predominating in the triethylene glycol ester of said half acid ester of Example 2.

USE OF THE ALKYLENE GLYCOL ESTER ADDITIVE IN LIQUID HYDROCARBON FUEL COMPOSITIONS

The ethoxylated ester reaction products of this invention can be incorporated into a wide variety of fuels for friction reducing activity.

When the products of this invention are used as multifunctional additives having dispersancy and friction reducing activities in petroleum fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

These middle distillate fuels are characterized generally by boiling within the range of about 120° to 500° C.

The ethoxylated ester additives may be conveniently dispensed as an additive concentrate of from 0.5 wt.% to 100wt.% with the balance conventionally an oleaginous material such as fuel or a mineral lubricating oil e.g. up to 99.5 weight percent, with or without other additives being present.

In the above compositions or concentrates, other conventional additives may also be present including dyes, detergents such as the reaction product of an aliphatic polyamine with an alkylated aryl carboxylic acid and antiicing additives, e.g. a hexylene glycol in gasolines and pour point depressants and cold flow improvers for the middle distillate fuels.

USE OF THE ALKYLENE GLYCOL-ESTER ADDITIVE IN LIQUID HYDROCARBON LUBRICATING OIL COMPOSITIONS

The alkylene glycol ester reaction products of this invention can be incorporated into lubricating oils to provide friction reducing activity. These lubricating oils require the presence of at least a friction reducing amount, e.g. from about 0.1 to 20, preferably 0.25 to 5% based on the total weight of the oil.

The hydrocarbons in which the additive of the invention is most effective are mineral oils having a viscosity as measured by ASTM D-445 of from about 2 to 40, preferably 5 to 20 centistokes at 99° C.

If the ethoxylated ester additive is used as an additive concentrate, the concentrate may consist essentially of from about 5 to 100 weight percent of said ethoxylated-ester additive, based on the total weight of said concentrate, the remainder being a suitable solvent such as kerosene, mineral oil, synthetic oil and a naphtha or the like. The preferred concentrate contains about 10–60 weight percent of said additive in the solvent.

In addition to the alkylene glycol ester additive, the lubricating oil composition contains other additives which provide for useful lubrication, such as ashless dispersants, metallic detergents, supplemental oxidation and corrosion inhibitors, extreme pressure agents, rust inhibitors, pour point depressants, viscosity index improvers, etc.

As used herein, the terminology "ashless dispersant" in describing a group of oil-soluble additives is intended to describe the now well-known class of non-metal-containing oil-soluble polymeric additives or the acyl derivatives of relatively high molecular weight carboxylic acids which are capable of dispersing contaminants and the like in hydrocarbons such as lubricating oils. The carboxylic acids may be mono- or polycarboxylic acids and they are generally characterized by substantially hydrocarbon constituents containing an average of 50 to 250 aliphatic carbon atoms.

A preferred class of ashless dispersants are the nitrogen-containing dispersant additives which are generally known in the art as sludge dispersants for crankcase motor oils. These dispersants include mineral oil-soluble salts, amides, imides and esters made from high molecular weight mono- and dicarboxylic acids (and where they exist the corresponding acid anhydrides) and various amines of nitrogen-containing materials having amino nitrogen or heterocyclic nitrogen and at least one amido or hydroxy group capable of salt, amide, imide or ester formation. Usually, these dispersants are made by condensing a monocarboxylic acid or a dicarboxylic acid or anhydride, preferably a succinic acid producing material such as alkenyl succinic anhydride, with an amine or alkylene polyamine. Usually, the molar ratio of acid or anhydride to amine is between 1:1 to 5:1, e.g. 1 moles of $C_{10}$–$C_{100}$ polyisobutenyl succinic anhydride to 1 mole of tetraethylene pentamine.

Primarily because of its ready availability and low cost, the hydrocarbon portion of the mono-, or dicarboxylic acid or anhydride is preferably derived from a polymer of a $C_2$ to $C_5$ monoolefin, said polymer generally having between 50 and 250 carbon atoms. A particularly preferred polymer is polyisobutylene.

Polyalkyleneamines are usually used to make the non-metal-containing dispersant. These polyalkyleneamines include those represented by the general formula:

wherein n is 2 to 3 and m is a number from 0 to 10. Specific compounds coming within the formula include diethylenetriamine, tetraethylenepentamine, dipropylenetriamine, octaethylenenonamine, and tetrapropylenepentamine; N,N-di-(2-aminoethyl) ethylenediamine may also be used. Other aliphatic polyamino compounds that may be used are N-aminoalkylpiperazines, e.g. N-(2-aminoethyl) piperazine. Mixtures of alkylene polyamines approximately tetraethylene pentamine are commercially available, e.g. Dow E-100 sold by Dow Chemical Company of Midland, Michigan.

Representative dispersants are formed by reacting about one molar amount of polyisobutenyl succinic anhydride with from about 0.25 to about one molar amount of tetraethylene pentamine or with from about 0.5 to 1.5 moles of a polyol, e.g. pentaerythritol.

It is possible to modify the ashless dispersants generally by the addition of boron in order to enhance the dispersancy of the additive. This is readily accomplished by adding boric acid to the reaction mixture after the imidation or esterification is substantially complete and heating the mixture at temperatures of 100° to 150° C. for a few hours.

Detergents useful in conjunction with dispersants, preferably the ashless type, include normal, basic or overbased metal, e.g. calcium, magnesium, etc., salts of petroleum naphthenic acids, petroleum sulfonic acids, alkyl benzene sulfonic acids, oil-soluble fatty acids, alkyl salicyclic acids, alkylene-bis-phenols, and hydrolyzed phosphorosulfurized polyolefins.

Oxidation inhibitors include hindered phenols, e.g. 2,6-ditert. butyl para-cresol, amines, sulfurized phenols and alkyl phenothiazines.

Pour point depressants include wax alkylated aromatic hydrocarbons, olefin polymers and copolymers, acrylate and methacrylate polymers and copolymers.

Viscosity Index Improvers include olefin polymers such as polybutene, ethylene-propylene copolymers, hydrogenated polymers and copolymers and terpolymers of styrene with isoprene and/or butadiene, polymers of alkyl acrylates or alkyl methacrylates, copolymers of alkyl methacrylates with N-vinyl 2-pyrrolidinone or dimethylaminoalkyl methacrylate, post-grafted polymers of ethylene-propylene with an active monomer such as maleic anhydride which may be further reacted with an alcohol or an alkylene polyamine, styrene/maleic anhydride polymers post-reacted with alcohols and amines, etc.

The invention will be further understood by reference to the following Examples which illustrates preferred forms of the invention and compares the same with unmodified, though similar compositions in friction reducing activity.

All of the Examples are illustrative and herein are not to be interpreted as specific limitations on this invention.

EXAMPLE 9

The product of Example 7 was evaluated in a formulated oil for its effect on friction in a ball-on-cylinder device as described in Technical Paper Series Paper 770376 entitled "The Use of Stimulant Devices to Evaluate the Wear Performance of Multigraded Engine Oils" by I. L. Goldblatt published by the Society of Automotive Engineers, Inc., 400 Commonwealth Drive, Warrendale, PA 15096. The ball-on-cylinder device consists basically of a 1.27 cm. diameter steel stationary ball which is loaded onto a 4.4 cm diameter rotating steel cylinder. A load of 2 Kg is applied to the end of a lever system having a 2:1 mechanical efficiency. The cylinder was rotated at 20 revolutions per hour for 1 hour in a test oil bath at 104° C. after said temperature of both has reached 104° C. and the coefficient determined.

As a comparative example, a multigraded oil containing no friction modifier was run. The concentration of the ethoxylated product in said multigraded oil was adjusted to provide two test systems, i.e. one containing 0.25 wt.% of the ethoxylated product of Example 7 and one containing 0.75 wt.% of said ethoxylated product of Example 7.

The multigraded lubricant composition was composed of the following:

| Component | Wt. % Active Ingredient |
|---|---|
| Dispersant | 2.5 |
| Magnesium Sulfonate (overbased) | 0.4 |
| Zinc dinonyl phenyl dithiophosphate | 1.0 |
| mineral oil | 96.1 |

The compounds of the invention were evaluated by subjecting the product of Example 7 to a study of its utility as a lubricity enhancing additive for lubricating oils by using said ball-on-cylinder test. The results of said tests are set forth in Table I.

TABLE I

| Test Sample | Wt % Product of Ex. 7 | Coefficient of Friction | % Reduction |
|---|---|---|---|
| 8-1 | 0 | 0.35 | |
| 8-2 | 0.25 | 0.13 | 63 |
| 8-3 | 0.75 | 0.10 | 71 |

From the Table, it is shown that the addition of the alkylene glycol ester of the invention to a formulated lubricating oil provides a significant reduction in coefficient of friction to said lubricating oil.

It is to be understood that the Examples present in the foregoing specification are merely illustrative of this invention and are not intended to limit it in any manner; nor is the invention to be limited by any theory regarding its operability. The scope of the invention is to be determined by the appended claims.

What is claimed is:

1. A composition comprising a major amount of liquid hydrocarbon lubricants and at least a friction-reducing amount of an alkylene glycol ester of an ester which is the reaction product of: (a) about 1 molar proportion of a hydrocarbyl substituted $C_4$ to $C_{10}$ dicarboxylic acid, anhydride or ester having about 6 to about 150 carbon atoms per hydrocarbyl group partly esterified with the reaction product of (b) either about 1 or 2 molar proportions of an aldehyde, or one molar proportion of ketone and one molar proportion of aldehyde, reacted with about 1 molar proportion of tris-(hydroxymethyl) aminomethane; said half ester reaction product having a 1-aza-3,7-dioxabicyclo[3.3.0]octyl ring.

2. A composition according to claim 1 wherein said hydrocarbyl substituted acid or anhydride is alkenyl succinic anhydride.

3. A composition according to claim 2 wherein said alkenyl group is octadecenyl.

4. A lubricating composition comprising a major amount of liquid lubricatng oil and in the range of about 0.1 to 20 wt.% of an alkylene glycol ester of a half ester which is the reaction product of: (a) about 1 molar proportion of a hydrocarbyl substituted $C_4$ to $C_{10}$ dicarboxylic acid, anhydride or ester having about 6 to about 150 carbon atoms per hydrocarbyl group partly esterified with the reaction product of (b) either about 1 or 2 molar proportions of an aldehyde, or one molar proportion of ketone and one molar proportion of aldehyde, reacted with about 1 molar proportion of tris-(hydroxymethyl) aminomethane; said reaction product having a 1-aza-3,7-dioxabicyclo[3.3.0] octyl ring.

5. A composition according to claim 4 wherein said alkylene glycol ester is the reaction product of one to ten moles of an ethoxylating agent to one mole of said half ester reaction product, said ethoxylating agent being of the class consisting of a $C_2$ to $C_3$ alkylene oxide and a glycol of the formula

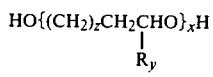

wherein x is 1 to 10, $R_y$ is hydrogen or methyl and z is 0 or 1.

6. A composition according to claim 5 wherein said alkylene glycol ester is of the formula

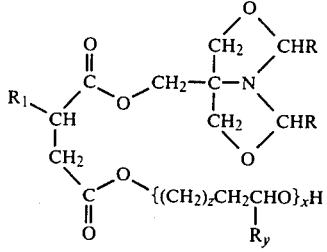

wherein X is 1 to 10, $R_1$ represents a hydrocarbyl group of 6 to 150 carbons, z is 0 or 1, R is H or $C_1$ to $C_{12}$ hydrocarbyl group and $R_y$ is H or a $CH_3$ group.

7. A composition according to claim 5 wherein said hydrocarbyl group contains about 12 to 24 carbon atoms.

8. A composition according to claim 7 wherein said hydrocarbyl substituted acid or anhydride is octadecenyl succinic anhydride and said ethoxylating agent is ethylene oxide.

9. A composition according to claim 7 wherein said aldehyde is formaldehyde.

10. An alkylene glycol ester of carboxylic half esters of 1-aza-3,7-dioxabicyclo[3.3.0] oct-5-yl methyl alcohol having the formula

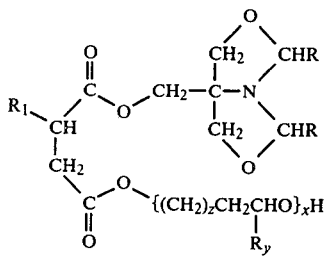

wherein X is 1 to 10, $R_1$ represents a hydrocarbyl group of 6 to 150 carbons, Z is 0 or 1, R is H or $C_1$ to $C_{12}$ hydrocarbyl group and $R_y$ is H or a $CH_3$ group.

* * * * *